US005700921A

United States Patent [19]
Westling et al.

[11] Patent Number: 5,700,921
[45] Date of Patent: Dec. 23, 1997

[54] LABELING NUCLEIC ACIDS

[75] Inventors: Mark E. Westling, San Mateo; Steven G. Daniel, Sunnyvale, both of Calif.

[73] Assignee: Vector Laboratories, Burlingame, Calif.

[21] Appl. No.: 562,650

[22] Filed: Nov. 27, 1995

[51] Int. Cl.$^6$ ............................ C12Q 1/68; C07H 21/02; C07H 19/00
[52] U.S. Cl. ..................... 536/22.1; 536/23.1; 536/24.3; 435/6
[58] Field of Search .......................... 536/22.1, 25.32; 436/6

[56] References Cited

U.S. PATENT DOCUMENTS

| | | | |
|---|---|---|---|
| 4,487,838 | 12/1984 | Hynes et al. | 435/504 |
| 4,711,955 | 12/1987 | Ward et al. | 536/29 |
| 4,737,454 | 4/1988 | Dattagupta et al. | 435/6 |
| 4,822,731 | 4/1989 | Watson et al. | 435/6 |
| 4,828,979 | 5/1989 | Klevan et al. | 435/6 |
| 4,898,951 | 2/1990 | Symons | 548/303 |
| 4,962,029 | 10/1990 | Levenson et al. | 435/192 |
| 5,047,519 | 9/1991 | Hobbs, Jr. et al. | 536/23 |

OTHER PUBLICATIONS

M. Wilchek and E.A. Bayer, "Introduction to Avidin–Biotin Technology", and Applications of Avidin–Biotin Technology: Literature Survey, In: *Methods in Enzymology*, (Wilchek and Bayer, eds.), vol. 184, (1990).

L. Klevan and Gulilat Gebeyehu, "Biotinylated Nucleotides for Labeling and Detecting DNA," In: *Methods in Enzymology* (Wilchek and Bayer, eds.), vol. 184, pp. 561–577 (1990).

L. Angerer et al., "An Electron Microscope Study of the Relative Positions of the 4S and Ribosomal RNA Genes in HeLa Cell Mitochondrial DNA," *Cell* 9, pp. 81–90, (1976).

T. Kempe et al., "Chemical and Enzymatic Biotin–Labeling of Oligodeoxyribonucleotides," *Nucleic Acids Res.* 13 pp. 45–57, (1985).

B.C.F. Chu and L.E. Orgel, "Laboratory Methods: Detection of Specific DNA Sequences With Short Biotin–Labeled Probes," *DNA* 4, pp. 327–331 (1985).

S.Y. Cheng et al., "A Versatile Method for the Coupling Protein to DNA: Synthesis of a Macroglobulin–DNA Conjugates," *Nucleic Acids Res.* 11, pp. 659–669 (1983).

B.A. Connolly, "Chemical Synthesis of Oligonucleotides Containing a Free Sulphydryl Group and Subsequent Attachment of Thiol Specific Probes," *Nucleic Acids Res.* 13, pp. 4485–4502, (1985).

R. Zuckermann et al., "Efficient Methods for Attachment of Thiol Specific Probes to the 3'—Ends of Synthetic Oligodeoxyribonucleotides," *Nucleic Acids Res.* 15, pp. 5305–5321, (1987).

B.C.F. Chu and L.E. Orgel, "Ligation of Oligonucleotides to Nucleic Acids or Proteins Via Disulfide Bonds," *Nucleic Acids Res.* 16, pp. 3671–3691, (1988).

M. Shimkus et al., "A Chemically Cleavable Biotinylated Nucleotide: Usefulness in the Recovery of Protein–DNA Complexes from Avidin Affinity Columns," *Proc. Natl. Acad. Sci. USA* 82, pp. 2593–2597, (1985).

A. Kallioniemi et al., "Comparative Genomic Hybridization for Molecular Cytogenetic Analysis of Solid Tumors," *Science* 258, pp. 818–821, (1992).

T. Ried et al., "Simultaneous Visualization of Seven Different DNA Probes by *in situ* Hybridization Using Combinatorial Fluorescence and Digital Imaging Microscopy," *Proc. Natl. Acad. Sci USA* 89, pp. 1388–1392, (1992).

C. Kessler, "Review: Non–Radioactive Analysis of Biomolecules," *Biotechnol.* 35, pp. 165–189, (1994); and.

J.G.J. Bauman et al., "Cytochemical Hybridisation with Fluorochrome—Labelled RNA," *Histochemistry* 73, pp. 181–193, (1981).

Matthews et al., Anal. Biochemistry 169: 1—25 (1988).

*Primary Examiner*—W. Gary Jones
*Assistant Examiner*—Ethan Whisenant
*Attorney, Agent, or Firm*—Medlen & Carroll, LLP

[57] ABSTRACT

Reagents and methods for multi-step labeling of nucleic acids allow the addition of relatively insoluble or unstable labels to nucleic acid in the final step. Nucleic acids can be stored as a stable intermediate capable of reacting with a label conjugated to a thiol-reactive group.

9 Claims, 1 Drawing Sheet

LABELING NUCLEIC ACIDS

FIELD OF THE INVENTION

The invention relates to nonradioactive labeling of nucleic acids, and, particularly, stepwise labeling providing intermediates which can be suitably stored or used with various detectable labels.

BACKGROUND

Molecular research involving genes from animal, plant and viral sources has burgeoned and has created a demand for new techniques and products for studying nucleic acids. One of the needs is for more flexible procedures to detect and isolate specific sequences of nucleic acid from among a mixture of components. This is important for medical diagnostic procedures and for research into new therapeutic products.

Researchers rely on labeled nucleic acid probes for the detection, isolation or localization of target nucleic acids which are of particular interest. The probe, which is a nucleic acid having a known or defined sequence, is capable of pairing with a target nucleic acid having a sequence that is complementary to that of the probe, a phenomenon known as nucleic acid hybridization. Hybridizing the target and probe nucleic acids allows the target to be detected or isolated in subsequent steps.

Initially, nucleic acid probes were labeled by incorporation of radioactive analogs of nucleotides. However, the use of radioactive analogs has numerous disadvantages, such as health hazards from exposure to radioactivity, problems in disposal of the radioactive molecules, and instability of the labeled probes.

More recently, a number of nonradioactive labels have been developed. A commonly used method of preparing nonradioactively labeled nucleic acid probes makes use of the strong noncovalent binding exhibited between molecules of biotin and avidin (U.S. Pat. No. 4,711,955 to Ward, D. C. et al., Dec. 8, 1987; U.S. Pat. No. 4,828,979 to Klevan, L. et al., May 9, 1989). First, biotin is incorporated into the nucleic acid probe and then the probe is bound to the target nucleic acid. After removal of the unbound probe, a detectable label that is conjugated to avidin is added and the strong specific binding interaction between biotin and avidin causes the avidin-conjugated label to become associated with the target nucleic acid (Wilchek, M. and Bayer, E. A., eds., 1990, Methods in Enzymology, Vol. 184).

Some procedures call for incorporating the biotin into nucleotides (the monomeric units of nucleic acid chains) and then enzymatically linking these nucleotide analogs into long chain nucleic acids ("polynucleotides"). However, the enzymatic methods have disadvantages: enzymes that require double-stranded template entail extra steps to isolate a single-stranded probe; enzymatic synthesis of labeled RNA probes is difficult; and large-scale enzymatic synthesis of labeled probes is comparatively expensive.

Non-enzymatic methods of labeling polynucleotides also have been developed. Various chemical reactions have been employed to covalently bond biotin to a polynucleotide probe (Angerer, L. et al., 1976, Cell 9, 81–90; Kempe, T. et al., 1985, Nucleic Acids Res. 13, 45–57; Chu, B. C. F. and Orgel, L. E., 1985, DNA 4, 327–331). One technique makes use of photoactivation to attach biotin to a polynucleotide (U.S. Pat. No. 4,898,951 to Symons, R. H., Feb. 6, 1990). The problem with the biotin methodology is that it is limited to use with labels conjugated to biotin's specific binding partner, avidin or streptavidin. The methodology is not interchangeable with other classes of label conjugates that are commercially available.

Other methods of labeling nucleic acids have employed a sulfur group for modifying the nucleic acid. The incorporation of disulfide or thiol groups into polynucleotide probes has been accomplished in a variety of ways including the reaction of glyoxyl derivatives with unpaired guanine residues (Cheng, S.-Y. et al., 1983, Nucleic Acids Res. 11, 659–669), the incorporation of sulfur-containing derivatives during oligonucleotide synthesis (Connolly, B. A., 1985, Nucleic Acids Res. 13, 4485–4502; Zuckermann, R. et al., 1987, Nucleic Acids Res. 15, 5305–5321; U.S. Pat. No. 4,962,029 to Levenson, C. et al., Oct. 9, 1990), the modification of the termini of oligonucleotides after synthesis (Chu, B. C. F. and Orgel, L. E., 1988, Nucleic Acids Res. 16, 3671–3691) or enzymatic incorporation of disulfide labeled nucleotides (Shimkus, M. et al., 1985, Proc. Natl. Acad. Sci. USA 82, 2593–2597). All these methods have the distinct disadvantage of being limited by the number and position of thiol moieties that can be incorporated into the nucleic acid and in the sequences which can be modified by thiol incorporation.

Another important aspect of probe technology is that the ability to use more than one label has become important in a number of applications such as nucleic acid sequencing (U.S. Pat. No. 5,047,519 to Hobbs, Jr., F. W. et al., Sep. 10, 1991), comparative genomic hybridization (Kallioniemi, A. et al., 1992, Science 258, 818–821) and gene mapping (Ried, T. et al., 1992, Proc. Natl. Acad. Sci. USA 89, 1388–1392). Commonly-used alternative nonradioactive labels include digoxigenin, dinitrophenyl (DNP), fluorescein (Kessler, C., 1994, J. Biotechnol. 35, 165–189) and enzymes used in conjunction with substrate.

Fluorescein is a commonly used label which can be used in two modes: it can be directly detected using the molecule's fluorescent properties or it can be detected by immunological methods using antibodies to the fluorescein molecule (Bauman, J. G. J. et al., 1981, Histochemistry 73, 181–193). This makes fluorescent labels useful for in situ detection of nucleic acid probes, and for chromosome mapping (Kessler). Thiol-reactive fluorescent probes are known which are fluorescent conjugates of iodoacetates and maleimides (Connolly, 1985, Nucleic Acids Research, 13: 4485–4502). However, use of fluorescein as a label is sometimes problematic because of difficulties in synthesizing a soluble form of the label and the possible effects of photoactivation on light-sensitive fluorochromes.

What is needed is a method of labeling polynucleotides which overcomes problems of instability of the bonds formed, insolubility of certain labels and limited number and location of sites for the label to be incorporated into a nucleic acid probe.

SUMMARY OF THE INVENTION

Figure 1:
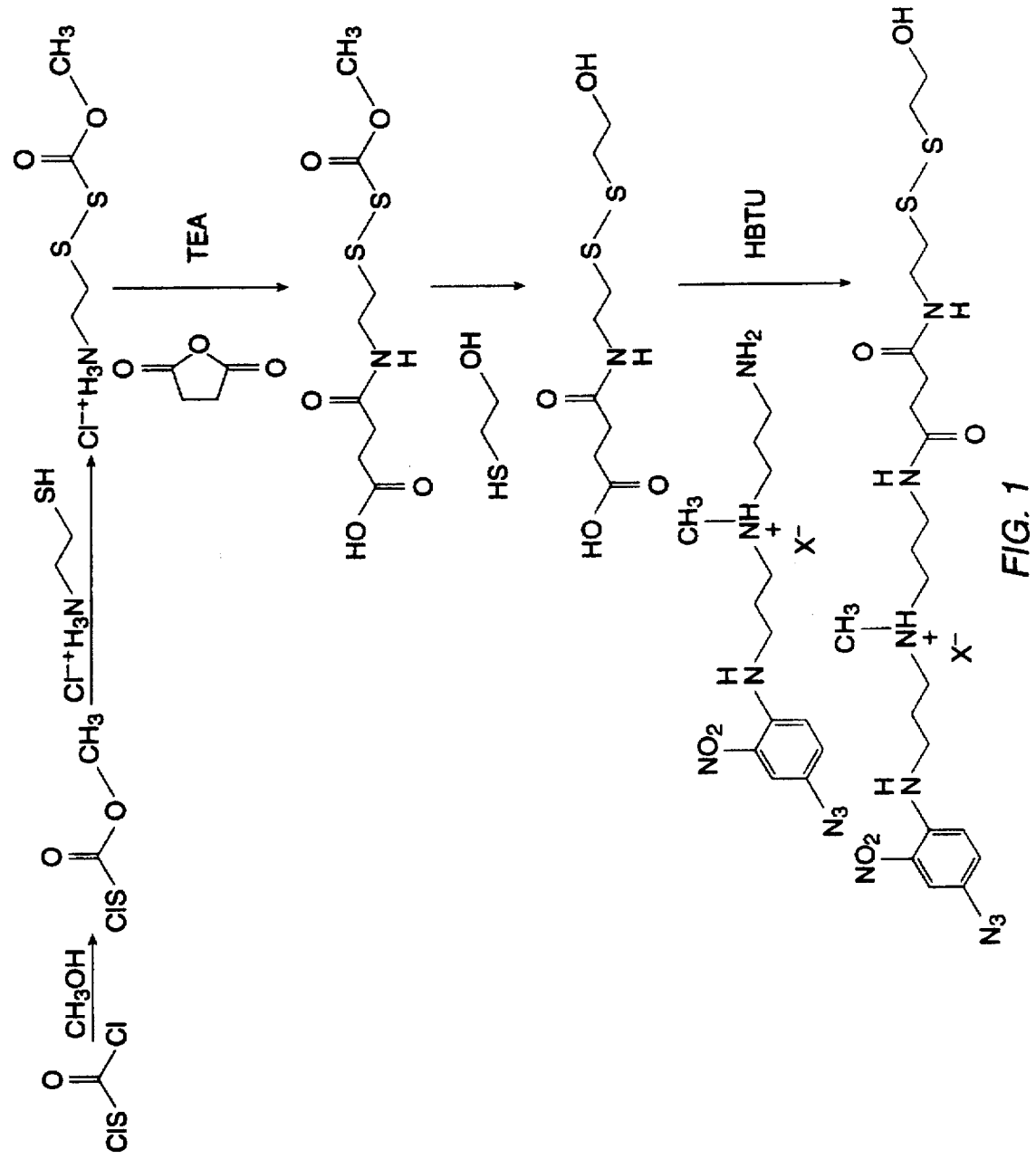
FIG. 1 is a scheme for preparing a photochemically activatable pro-thiol aryl azide.

A new class of nucleic acid probes is described which is prepared from a nucleic acid tagged with an aryl azide containing a protected thiol. After deprotection of the thiol, a label conjugated to a thiol-reactive group is then covalently bound to the nucleic acid. As used herein, a label is a detectable moiety or a ligand. Activation of the pro-thiol aryl azide couples a pro-thiol to the nucleic acid which, when deprotected permits the use of a wide spectrum of labels so long as the label is conjugated to a thiol-reactive moiety. The labeled nucleic acids provided by this invention have broad utility as probes for biomedical research and DNA technology.

The invention contemplates a pro-thiol aryl azide for coupling a thiol group to a nucleic acid. The pro-thiol aryl azide has the structure:

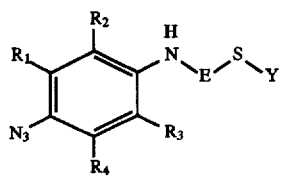

wherein, $R_1$ to $R_4$, which may be the same or different, are selected from the group consisting of H, alkyl, nitro, hydroxy, halide, carboxylic acid, methoxy, cyano, amino groups and salts thereof; wherein E is a chain of $C_1$–$C_{20}$ having chain constituents selected from the group consisting of alkyl, alkenyl, alkynyl, heteroatoms and salts thereof, said chain constituents having substituents selected from the group consisting of H, $C_1$–$C_6$ alkyl, aryl, ester, ether, amine, amide, halo groups and salts thereof; and wherein Y is a group capable of protecting the sulfur moiety from chemical reaction and removable so as to generate a thiol moiety. In one embodiment, $R_1$, $R_2$ and $R_4$ are hydrogen and $R_3$ is —$NO_2$. In another embodiment the heteroatoms are selected from the group consisting of N, O and S.

The Y group of the pro-thiol aryl azide is selected from the group consisting of:

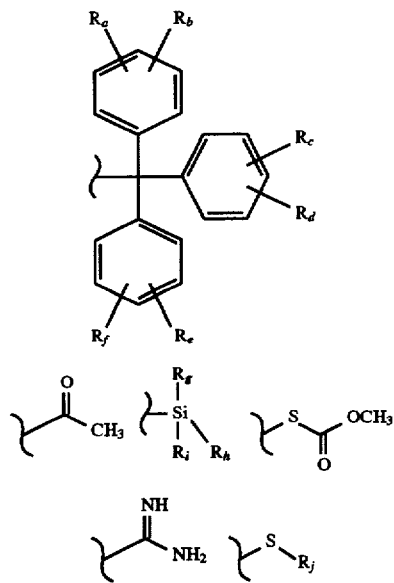

wherein, $R_a$, $R_b$, $R_c$, $R_d$, $R_e$ and $R_f$ which may be the same or different, are selected from the group consisting of hydrogen, alkyl of 1 to 6 carbons or alkoxy of 1 to 6 carbons; wherein $R_g$, $R_h$ and $R_i$, which may be the same or different, are selected from the group consisting of alkyl of 1 to 6 carbons and aryl; and wherein $R_j$ is selected from the group consisting of alkyl, aryl, alkyl containing heteroatoms or aryl containing heteroatoms.

In a preferred embodiment of the pro-thiol aryl azide, E is:

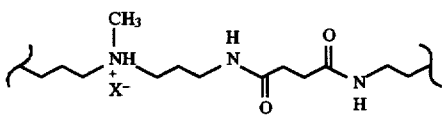

and Y is:

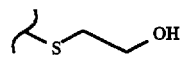

The invention also contemplates a method for modifying a nucleic acid comprising: (a) contacting a nucleic acid with a pro-thiol aryl azide having the structure:

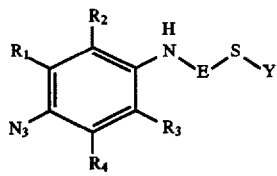

and salts thereof, wherein, $R_1$ to $R_4$, which may be the same or different, are selected from the group consisting of H, alkyl, nitro, hydroxy, halide, carboxylic acid, methoxy, cyano, and amino groups; wherein E is a chain of $C_1$–$C_{20}$ having chain constituents selected from the group consisting of alkyl, alkenyl, alkynyl and heteroatoms, said chain constituents having substituents selected from the group consisting of H, $C_1$–$C_6$ alkyl, aryl, ester, ether, amine, amide and halo groups; and wherein Y is a group capable of protecting the sulfur moiety from chemical reaction and removable so as to generate a thiol moiety; and (b) subjecting the nucleic acid and the pro-thiol aryl azide to activation conditions sufficient to cause a reaction therebetween. In one embodiment, step (b) comprises photoactivating the pro-thiol aryl azide in the presence of the nucleic acid. In another embodiment, the method further comprises: (c) removing unreacted pro-thiol aryl azide; and (d) removing the protecting group Y to form an intermediate having the structure:

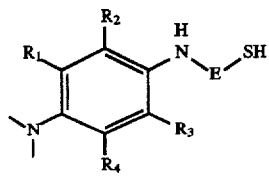

NUCLEIC ACID

The invention contemplates an embodiment wherein the method for modifying a nucleic acid further comprises: reacting the intermediate formed in step (d) with a label conjugated to a thiol-reactive group whereby a labeled nucleic acid results having the structure:

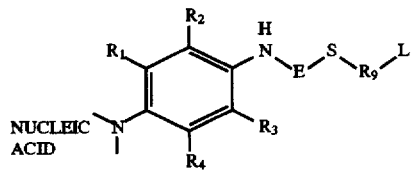

wherein $R_9$ is the thiolated conjugate of the thiol-reactive group and L is selected from the group consisting of a ligand or a detectable label. In one embodiment, L is selected from the group consisting of fluorophores, biotin and fucose. In one embodiment, the thiol-reactive group is selected from the group consisting of maleimides, iodoacetamides, pyridyl disulfides, vinyl pyridines, vinyl sulfones, acrylates, aryl mercurial compounds and aziridino compounds covalently linked to the detectable label or ligand. In another embodiment, L is fluorescein and the thiol-reactive group is a maleimide.

The invention contemplates a covalent conjugate of a nucleic acid and a thiol-reactive label having a thiol-reactive group given by the structure:

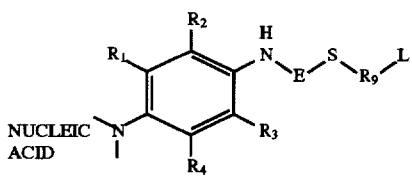

wherein, $R_1$ to $R_4$, which may be the same or different, are selected from the group consisting of H, alkyl, nitro, hydroxy, halide, carboxylic acid, methoxy, cyano, amino groups and salts thereof; wherein E is a chain of $C_1$–$C_{20}$ having chain constituents selected from the group consisting of alkyl, alkenyl, alkynyl, heteroatoms and salts thereof, said chain constituents having substituents selected from the group consisting of H, $C_1$–$C_6$ alkyl, aryl, ester, ether, amine, amide, halo groups and salts thereof; wherein $R_9$ is the thiolated conjugate of the thiol-reactive group; and wherein L is selected from the group consisting of a ligand or a detectable label.

The present invention also contemplates a labeling kit for labeling a nucleic acid, wherein the labeling kit comprises: a) a pro-thiol aryl azide having the structure:

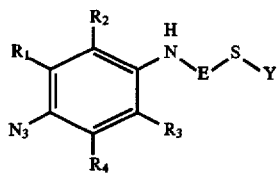

and salts thereof, wherein, $R_1$ to $R_4$, which may be the same or different, are selected from the group consisting of H, alkyl, nitro, hydroxy, halide, carboxylic acid, methoxy, cyano, and amino groups; wherein E is a chain of $C_1$–$C_{20}$ having chain constituents selected from the group consisting of alkyl, alkenyl, alkynyl and heteroatoms, said chain constituents having substituents selected from the group consisting of H, $C_1$–$C_6$ alkyl, aryl, ester, ether, amine, amide and halo groups; and wherein Y is a group capable of protecting the sulfur moiety from chemical reaction and removable so as to generate a thiol moiety; b) a reagent to remove the protecting group so as to generate a terminal thiol; and c) a thiol-reactive label or ligand capable of reacting with the thiol.

In one embodiment of the labeling kit, the pro-thiol aryl azide has the structure:

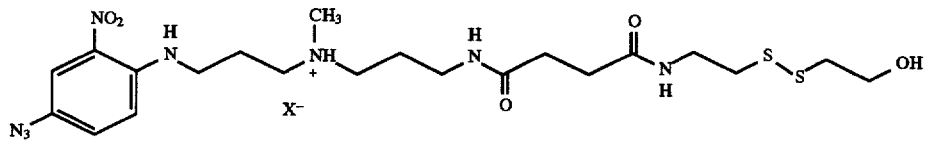

DETAILED DESCRIPTION OF THE INVENTION

According to the present invention, a pro-thiol aryl azide is provided having a hydrophilic spacer arm terminated by a protected sulfur moiety. The pro-thiol aryl azide is stable in the dark and, upon activation, forms a highly reactive aryl nitrene. The nitrene is reactive with nucleic acid. The pro-thiol aryl azide also may be used to modify other polymers such as proteins or carbohydrates.

As used herein a "nucleic acid" is a nucleotide polymer and may be single-stranded, double-stranded or triple-stranded. An "oligonucleotide," as used herein, is a molecule comprised of two or more deoxyribonucleotides or ribonucleotides and is typically single-stranded and of from about 2 to about 400 monomer units, and, typically for most probe-based applications, from about 2 to about 100 monomer units. It is to be understood that the reagents and methods of the present invention may be used in conjunction with short oligonucleotides as well as with a full-length polynucleotide strand. The nucleic acids may be native sequences or they may be derived synthetically or by cloning.

The pro-thiol aryl azide is useful for indirect (stepwise) labeling of nucleic acids and overcomes problems encountered when attempting to directly label nucleic acids with labels having limited solubility and sensitivity to photoactivation. For example, the synthesis and use of photoactivatable forms of fluorescein is difficult due to problems of insolubility of a photoactivatable fluorescein in aqueous systems. The present invention overcomes this difficulty by performing the photoactivation on the pro-thiol aryl azide, so as to introduce a thiol into a nucleic acid; the thiol-protecting group is then removed to expose a reactive thiol, and the thiol is reacted with a thiol-reactive fluorescein label.

As used herein, "photoactivation" refers to subjecting the pro-thiol aryl azide to light, which results in its conversion from an azide to a nitrene compound. The nitrene inserts into the bonds of the nucleic acid. In this manner, the protected sulfur moiety, on one end of the spacer arm is coupled to the nucleic acid.

A nucleic acid tagged with the pro-thiol of this invention is a universal acceptor for a variety of labels so long as the label is conjugated to a thiol-reactive moiety. Suitable thiol-reactive groups include, but are not limited to, maleimides, iodoacetamides, pyridyl disulfides, vinyl pyridines, acrylates, and aryl mercurial and aziridino derivatives. A thiol-reactive group may be incorporated into a particular label using standard chemical techniques.

The labeled nucleic acid of this invention is capable of long-term storage because of the stability of the bonds formed after modification with the pro-thiol aryl azide. A nucleic acid labeled in this manner (and rendered single-stranded, in the case of double- or triple-stranded nucleic acid) is useful as a nucleic acid probe for hybridization reactions. Nucleic acids labeled in this manner could also be used in the isolation and purification of target nucleic acid sequences and in the enhanced uptake of nucleic acids by living cells.

As used herein a "nucleic acid probe" is a labeled nucleic acid of defined base sequence or a labeled synthetic nucleic acid analog which is capable of hybridizing with a nucleic acid having a complementary sequence. The complementary sequence is referred to as the "target sequence" and the nucleic acid containing that sequence is referred to as the "target nucleic acid." Target nucleic acids for use with this invention include double stranded or single stranded DNA and RNA. The nucleic acids may include native, recombinant, or synthetic target sequences. These include, but are not limited to genomic DNA, cDNA, and mRNA. A "hybridized nucleic acid probe" refers to a nucleic acid probe that is paired to its target sequence by the formation of hydrogen bonds between the defined and target sequences.

1. Structure of the Pro-Thiol Aryl Azide

The first aspect of the present invention is the provision of a compound for derivatizing a nucleic acid to incorporate a protected thiol moiety. The compound has the structure shown in formula (1):

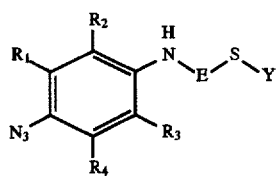

The substituents, $R_1$ to $R_4$, are, independently, H, alkyl, nitro, hydroxy, halide, carboxylic acid, methoxy, cyano or amino groups. The present invention further includes the salts of the compounds of formula (1). The dihydrogen citrate salt is preferred. E is a straight-chained alkyl, $C_1$–$C_{20}$, optionally containing within the chain double bonds, triple bonds, aryl groups and/or heteroatoms including, but not limited to N, O or S, wherein the heteroatoms can be part of such functional groups as ethers, thioethers, esters, amines or amides, wherein substituents on E, which may contain heteroatoms, can include $C_{1-6}$ alkyl, aryl, ester, ether, amine, amide or halo groups. Y is a group which is capable of protecting the sulfur moiety from chemical reaction and can be removed to generate a thiol moiety. The protection is afforded by a "protecting group" such that the resulting protected sulfur is not susceptible to chemical reaction during the coupling of the pro-thiol aryl azide to a nucleic acid.

It is contemplated that the protecting group provides for a pro-thiol aryl azide that is stable in aqueous solution and preferably retains stability over an extended period. Appropriate sulfur protecting groups (Y) are shown as follows (2-7):

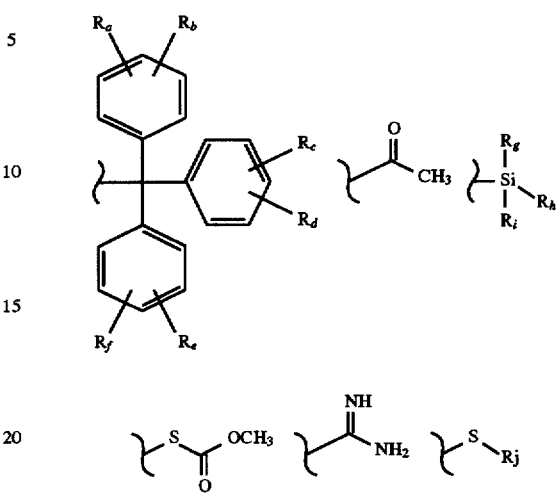

wherein, $R_a$, $R_b$, $R_c$, $R_d$, $R_e$ and $R_f$ are, independently, hydrogen, alkyl of about 1 to 6 carbons or alkoxy of about 1 to 6 carbons; $R_g$, $R_h$ and $R_i$, which may be the same or different, are alkyl of 1 to 6 carbon atoms or aryl, such as diphenyl t-butyl, di-t-butyl phenyl and dimethyl phenyl; and $R_j$ is alkyl, aryl, such as phenyl, alkyl containing heteroatoms or aryl containing heteroatoms, such as pyridyl. It is to be understood that the aforementioned exemplary protecting groups are illustrative only and that other appropriate sulfur protecting groups may be used.

Preferred protecting groups are those wherein, subsequent to their removal, high incorporation of label is attainable for the thiol-tagged nucleic acid. Ease of removal and good solubility are characteristics that are desired. A preferred embodiment of the protected pro-thiol aryl azide is shown in formula (8):

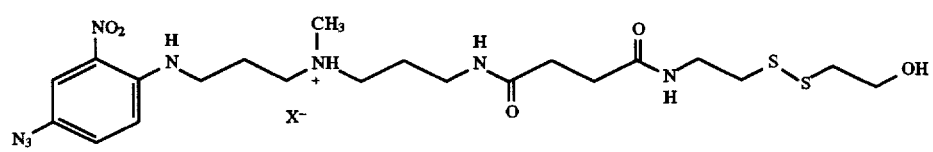

2. Preparation of the Pro-Thiol Aryl Azide

The second aspect of the present invention is a process for preparing a compound represented by formula (1):

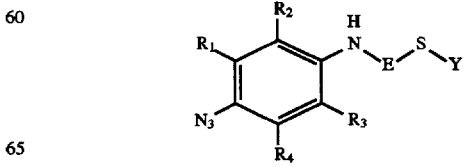

wherein $R_1$ to $R_4$, are, independently, H, alkyl, nitro, hydroxy, halide, carboxylic acid, methoxy, cyano or amino substituents or the salts of thereof. E is a straight-chained alkyl, $C_1-C_{20}$, optionally containing within the chain double bonds, triple bonds, aryl groups and/or heteroatoms including, but not limited to N, O or S, wherein the heteroatoms can be part of such functional groups as ethers, thioethers, esters, amines or amides, wherein substituents on E, which may contain heteroatoms, can include $C_1-C_6$ alkyl, aryl, ester, ether, amine, amide or halo groups. Y is a group capable of protecting the sulfur moiety from chemical reaction and can be removed to generate a thiol moiety. The process comprises reacting a compound represented by formula (9):

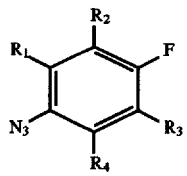

wherein $R_1$ to $R_4$ have the meanings defined above, with a compound represented by formula (10):

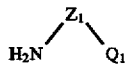

wherein $Z_1$ is a straight-chained $C_1-C_{20}$ alkyl, optionally containing within the chain double bonds, triple bonds, aryl groups and/or heteroatoms including, but not limited to N, O or S, wherein the heteroatoms can be part of such functional groups as ethers, thioethers, esters, amines or amides, wherein substituents on $Z_1$, which may contain heteroatoms, can include $C_1-C_6$ alkyl, aryl, ester, ether, amine, amide or halo groups and wherein $Q_1$ is a reactive group including but not limited to a carboxylic acid, a primary amine, a halomethylcarbonyl, a hydrazine, an acyl hydrazide, an olefin, or an N-maleimide; to produce a compound represented by formula (11):

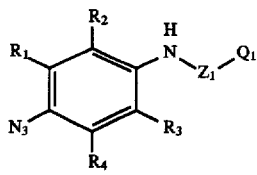

wherein $R_1$ to $R_4$, $Z_1$ and $Q_1$ have the meanings defined above. This compound is then reacted with a compound represented by formula (12):

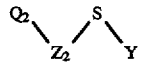

wherein $Z_2$ is a straight-chained alkyl, $C_1-C_{20}$, optionally containing within the chain double bonds, triple bonds, aryl groups and/or heteroatoms including, but not limited to N, O or S, wherein the heteroatoms can be part of such functional groups as ethers, thioethers, esters, amines or amides, wherein substituents on $Z_2$, which may contain heteroatoms, can include $C_1-C_6$ alkyl, aryl, ester, ether, amine, amide or halo groups; $Q_2$ is a reactive group including but not limited to a carboxylic acid, an acid halide, an activated ester, an iminoester, a primary amine, a mixed anhydride, an acyl imidazole, an N-(carbonyloxy)imide, an aldehyde, a halomethylcarbonyl, a hydrazine, an acyl hydrazide, an olefin, an epoxide or an N-maleimide; to produce a compound represented by formula (1).

In a particularly preferred embodiment of this process, the compound having the structure shown in formula (8) is prepared according to the scheme shown in FIG. 1. TEA is triethylamine, and HBTU is the coupling reagent, O-benzotriazol-1-yl-N, N,N',N'-tetramethyluronium hexafluorophosphate (Aldrich Chemical Co).

3. Method for Use of the Pro-Thiol Aryl Azide

The third aspect of the present invention is a method of introducing a detectable label into a nucleic acid in a stepwise manner via a photoreactive pro-thiol aryl azide having the structure shown in formula (1). The nucleic acid selected for labeling is generally a single or double strand sequence of deoxyribonucleic acid (DNA), or ribonucleic acid (RNA) or may also be a synthetic oligonucleotide analog capable of hybridizing to target nucleic acids in a sequence-specific manner. The nucleic acid is contacted with the compound of formula (1). The mixture is subjected to activation conditions resulting in a compound as shown in formula (13):

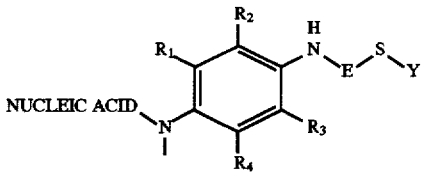

wherein $R_1$ to $R_4$, E and Y are as described above. The pro-thiol is bound to a residue of the nucleic acid. The precise nature of the bond is not understood.

The methods for activating aryl azides are generally known and include, e.g., photolysis, thermolysis, and transitional metal catalysis. Aryl azides can be activated by exposure to U.V. or visible light, by irradiation with light sources such as fluorescent lamps, mercury vapor lamps or photographic flash bulbs. Additionally, activation will occur by heating (e.g. 95° C. for 10 min) or by incubation with salts of transition metals (e.g. at 37° C. for 60 min). Photoactivation is the preferred method.

Unreacted components are removed by solvent extraction. The compound of formula (13) is then contacted with reagents specific for the removal of group Y under appropriate conditions to generate the compound of formula (14):

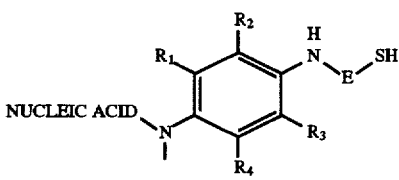

wherein $R_1$ to $R_4$ and E are as described above. Reagents and conditions for the removal of the particular protecting groups are generally well known.

The compound having the structure shown in formula (14) is then contacted with a thiol-reactive form of a label or ligand so as to form a labeled nucleic acid probe having the structure shown in formula (15):

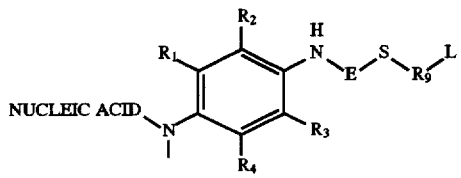

wherein $R_1$ to $R_4$, and E are as described above; $R_9$ is the thiolated conjugate of the thiol-reactive group in the thiol-reactive label and L is a detectable label or ligand. Suitable labels or ligands include, but are not limited to, enzymes (such as peroxidase or alkaline phosphatase), enzyme cofactors, enzyme inhibitors, sugars, radioisotopes, chemiluminescent compounds, chromophores, fluorophores, scintillants, avidin or streptavidin binding molecules and the like. Suitable thiol-reactive groups include maleimides, iodoacetamides, pyridyl disulfides, vinyl pyridines, vinyl sulfones, acrylates, aryl mercurial compounds and aziridino compounds covalently linked to the detectable label or ligand.

The method is suitable for labeling a wide variety of nucleic acids and synthetic nucleic acids. Synthetic nucleic acid analogs that would be useful for labeling include, but are not limited to, peptide nucleic acids, phosphorothioates and the like which are capable of hybridizing to target nucleic acids in a sequence-specific manner. Such synthetic molecules often have the phosphodiester bond in DNA or RNA replaced by a different linkage.

In a preferred embodiment of this method, the compound having the structure shown in formula (8) is mixed with a nucleic acid in water and irradiated with visible light on ice. The reaction mixture is extracted with 2-butanol and the sulfur protecting group is removed by reaction with tris(2-carboxyethyl)phosphine (TCEP) to give a compound with the structure shown in formula (16):

The thiol-tagged nucleic acid probe shown in formula (16) is then reacted with fluorescein-5-maleimide

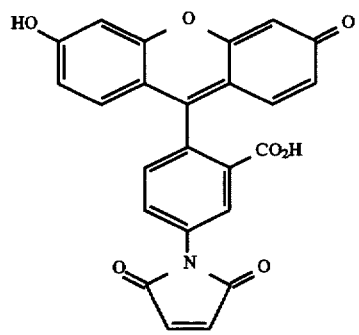

to form a fluorescein-labeled nucleic acid probe with the structure shown in formula (17):

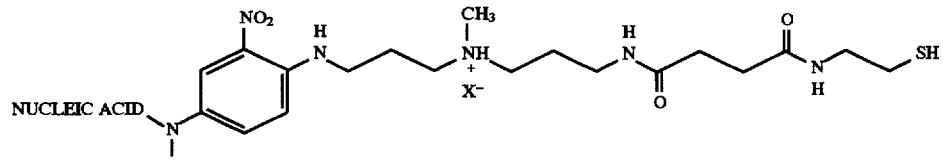

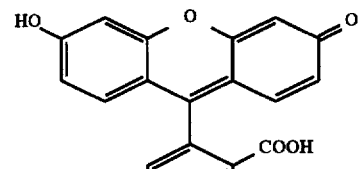

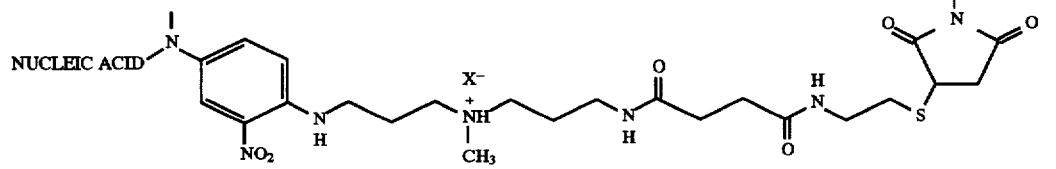

The fluorescein-labeled nucleic acid probe may then be isolated from the reaction mixture by common methods of nucleic acid isolation well-known to one skilled in the art, including, but not limited to, ethanol precipitation at low temperatures.

4. A Labeled Nucleic Acid Probe

A fourth aspect of the present invention is the labeled nucleic acid represented by formula (15):

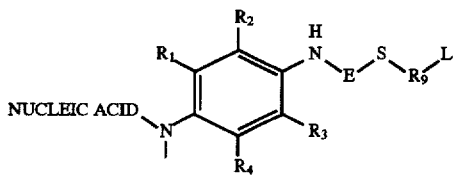

wherein, $R_1$ to $R_4$, which may be the same or different, are selected from H, alkyl, nitro, hydroxy, halide, carboxylic acid, methoxy, cyano or amino groups or salts thereof; E is a straight-chained alkyl, $C_1$–$C_{20}$, optionally containing within the chain double bonds, triple bonds, aryl groups and/or heteroatoms including, but not limited to N, O or S, wherein the heteroatoms can be part of such functional groups as ethers, thioethers, esters, amines or amides, wherein substituents on E, which may contain heteroatoms, can include $C_1$–$C_6$ alkyl, aryl, ester, ether, amine, amide or halo groups; and $R_9$ is the thiolated form of the thiol-reactive group in the thiol-reactive label and L is a detectable label or ligand.

A labeled nucleic acid probe, labeled according to the present invention, is intended for the detection, quantification or isolation of specific nucleic acid sequences in a specimen. The labeled nucleic acid probe is selected to form a detectable complex with the nucleic acid sequence of interest. For use in hybridization, the labeled nucleic acid probe is diluted in hybridization buffer and used in accordance with standard hybridization techniques (see e.g. Sambrook, J. et al., 1989, Molecular Cloning, Cold Spring Harbor Laboratory Press). The general procedure followed is well known in the art and typically involves: (1) providing a labeled nucleic acid probe, which has a nucleotide sequence sufficiently complementary to that of an analyte of interest to enable hybridization; (2) contacting the analyte of interest with the labeled nucleic acid probe; (3) separating bound and free nucleic acid probe and (4) detecting the presence of or isolating target nucleic acid complexes which form, by detecting or binding the label or ligand which is attached to the nucleic acid probe.

In one embodiment of this process, the labeled nucleic acid probe has a structure as shown in formula (17) and, after hybridization to an analyte which is attached to a solid support, the target nucleic acid complexes are detected by binding an antifluorescein antibody, which has been covalently coupled to alkaline phosphatase, to the fluorescein-labeled nucleic acid probe. The presence of the enzyme is then localized using a precipitating, colorimetric substrate for alkaline phosphatase. Detecting fluorescein by the antifluorescein antibody method allows for amplifying the detectable signal. Alternatively, fluorescein may be detected by measuring the degree of fluorescence that can be induced.

A labeled nucleic acid probe may be generated efficiently when a nucleic acid of interest is used in conjunction with a labeling kit. The labeling kit comprises the pro-thiol aryl azide of this invention, a reagent to remove the protecting group so as to generate a terminal thiol, and a thiol-reactive label or ligand capable of reacting to the thiol. The kit may additionally contain the appropriate buffers for the thiol-tagging and labeling reactions or a labeled nucleic acid for use as a standard.

The invention described above provides a novel way to label nucleic acid probes and has numerous advantages compared to existing methods. The pro-thiol aryl azides are easily synthesized and their coupling to nucleic acids is simple and rapid. The chemical attachment of a wide range of labels is not restricted by the narrow substrate specificities of nucleic acid synthetic enzymes used in most techniques. Once a particular nucleic acid has been tagged with the pro-thiol, it can be stored prior to removal of the group protecting the sulfur moiety. Subsequently, aliquots of the thiol-tagged nucleic acid can be labeled with several different thiol-reactive labels, as and when required. Use of the pro-thiol aryl azide provides an economical method of labeling large amounts of nucleic acids which is important in the preparation of probe-based diagnostic kits. The method described above also has the advantage of being able to label DNA or RNA, either single or double stranded, using the same pro-thiol aryl azide and procedure. In short, the present invention combines the simplicity of aryl azide chemistry with the utility of multiple labels and ligands.

The thiol-tagged compounds of this invention can be put to additional uses by conjugating the reactive thiol to an appropriate material having a thiol-reactive group. For example, the thiol-tagged compounds can be immobilized on a column for solid phase chromatography by reacting the thiol-reactive compound with a column matrix having thiol-reactive groups.

It is to be understood that while the invention has been described in conjunction with the preferred embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXPERIMENTAL

The following examples serve to illustrate certain preferred embodiments and aspects of the present invention and are not to be construed as limiting the scope thereof.

In the disclosure which follows, the following abbreviations apply: temp. (temperature); °C. (degrees Centigrade); M (molar); mmol (millimoles); ml (milliliters); μl (microliters); g (grams); mg (milligrams); μg (micrograms); ng (nanograms); pg (picograms); v/v (volume to volume); w/v (weight/volume); cm (centimeters); min (minutes); TLC (thin layer chromatography); AcOH/H$_2$O (acetic acid/water ); Rf (ratio of movement of the band to the front of the solvent ); NMR (nuclear magnetic resonance spectrophotometry); CDCl$_3$/TMS (deuterated chloroform/tetramethyl silane); bp (boiling point); IR (infrared); eq (equivalents); N (normal); Tris (Tris(hydroxymethyl) aminomethane buffer); TCEP (tris(2-carboxyethyl) phosphine); DMSO (dimethylsulfoxide); DMF (N,N-dimethylformamide); xg (times the force of gravity); 1x(one-fold); DNA (deoxyribonucleic acid); λ Hind III DNA (Lambda DNA Hind III digest); TE (tris EDTA); SSC (saline sodium citrate buffer); Tween 20 (TWEEN 20); PBST (phosphate buffered saline/Tween-20); TBST (Tris-buffered saline/Tween 20); BCIP/NBT alkaline phosphatase dye substrate (5-bromo-4-chloro-3-indolyl phosphate/nitro blue tetrazolium); TBE (Tris borate EDTA buffer); V (volts); EDTA (ethylenediaminetriacetic acid); ABC-AP reagent (avidin-biotin complex-alkaline phosphatase). All NMR were performed on a Bruker AC 300 MHz NMR spectrophotometer and all IR measurements were made on a Perkin-Elmer PE 1310 IR spectrophotometer.

EXAMPLE 1

Synthesis of N-(3-aminopropyl)-N'-(4-azido-2-nitrophenyl)-N-methyl- 1,3-propanediamine

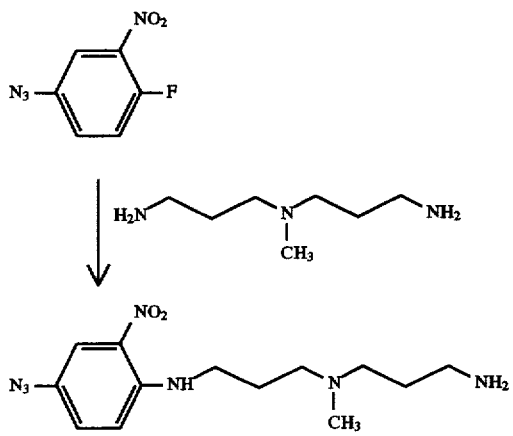

The reaction was carried out in the dark. A solution of 4-fluoro-3-nitrophenyl azide (0.91 g, 5.0 mmol, Sigma) in 10 ml dry ether was added dropwise with stirring to a solution of 3.2 ml of N-(3-aminopropyl)-N-methyl-1,3-propanediamine (10 mmol, Aldrich) in 20 ml dry ether and the mixture was stirred for 30 min. The reaction was monitored using TLC (alumina, elution with methanol). The solvent was removed and the red oil was dissolved in 25 ml water, 25 ml 1.0M NaOH and then extracted into ethyl acetate (2×50 ml). The organic phase was dried over $MgSO_4$ and the solvent then removed in vacuum. TLC: (I) alumina, eluted with methanol, Rf=0.43 (II) silica gel, elution with 1:9 AcOH/$H_2O$, Rf between Rf=0.23 and Rf=0.55. $^1H$ NMR ($CDCl_3$/TMS) δ: 1.45 (2H, broad s, NH), 1.64 (2H, m, $CH_2$), 1.87 (2H, p, J=6.52 Hz, $CH_2$), 2.25 (3H, s, $CH_3$), 2.43 (2H, t, $CH_2$), 2.47 (2H, t, J=6.46 Hz, $CH_2$), 2.73 (2H, t, J=6.89 Hz, $CH_2$), 3.37 (2H, m, J=6.61 Hz, $CH_2$), 6.89 (1H, d, J=9.23 Hz, ArH), 7.10 (1H, dd, J=2.73, 9.20 Hz, ArH), 7.79 (1H, d, J=2.74 Hz, ArH), 8.47 (1H, m, NH). $^{13}C$ NMR ($CDCl_3$/TMS) δ: 143.23 (Q), 131.24 (Q), 127.91 (CH), 127.16 (Q), 115.73 (CH), 115.44 (CH), 55.70 ($CH_2$), 55.40 ($CH_2$), 42.03 ($CH_2$), 41.90 ($CH_3$), 40.50 ($CH_2$), 30.94 ($CH_2$), 26.20 ($CH_2$).

EXAMPLE 2

Synthesis of (methoxycarbonyl)sulfenyl chloride

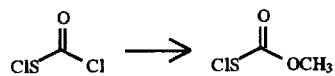

(Methoxycarbonyl)sulfenyl chloride was prepared by adding 5.24 g MeOH (164.06 mmol) in 12 ml of ether dropwise to a solution of 21.47 g (chlorocarbonyl)sulfenyl chloride (164.02 mmol, Aldrich) in 60 ml of ether over 1 hour at 25° C. The mixture was stirred at 25° C for 23 hours and then concentrated carefully on a rotary evaporator. The crude ester was purified by vacuum distillation (bp. 67°–68° C./74 torr) to give 17.86 g (86%) of the pure ester. IR (neat) cm$^{-1}$: 2975, 1760 (b), 1440, 1320, 1300, 1220–1120 (b), 940, 820. $^1H$ NMR ($CDCl_3$) δ: 3.98 (3H, s, $CH_3$). $^{13}C$ NMR ($CDCl_3$/TMS) δ: 167.62 (Q), 56.09 ($CH_3$).

EXAMPLE 3

Synthesis of (methoxycarbonyldithio)ethylamine hydrochloride

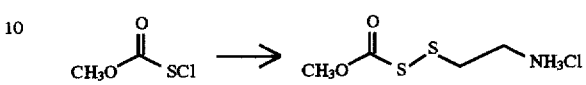

A round bottomed flask charged with 8.13 g of (methoxycarbonyl)sulfenyl chloride (1.1 eq., 64.3 mmole) in 32 ml anhydrous methanol and was cooled to 0° C. To this, a solution of 6.64 g aminoethanethiol hydrochloride (1 eq., 58.5 mmole, Aldrich) in 30 ml anhydrous methanol was added dropwise over a 30 min period and then the reaction mixture was allowed to warm to room temperature. After stirring at this temperature for an additional 2 hours, the reaction was stripped of volatiles in vacuo to give a white solid. The residue was then taken up in a minimal mount of hot methanol and treated with diethyl ether until the solution became turbid, at which point the solution was stored at −20° C. The next day the mixture was filtered, yielding 9.66 g (82%) as a pure white solid. $^1H$ NMR ($D_2O$/TMS) δ3.14 (2H, t, J=6.28 Hz, $CH_2$), 3.24 (2H, t, J=6.23 Hz, $CH_2$), 3.95 (3H, s, $CH_3$), 4.81 (3H t, J=0.53 Hz, $NH_3$). $^{13}C$ NMR ($D_2O$/TMS) δ: 35.83 ($CH_2$), 37.95 ($CH_2$), 56.97 ($CH_3$), 172.76 (Q).

EXAMPLE 4

Synthesis of (methoxycarbonyldithio) ethylamidosuccinic acid

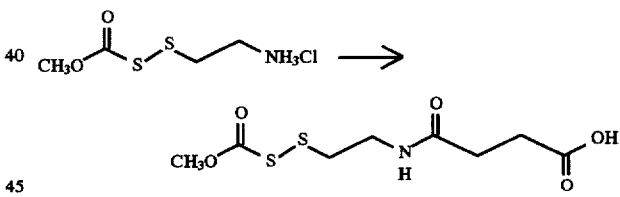

A round bottomed flask was charged with 1.63 g (1 eq., 0.008 mole) (methoxycarbonyldithio)ethylamine hydrochloride in 10 ml DMF, then treated with 0.84 g (1.05 eq., 8.4 mmole) succinic anhydride (Aldrich) in 10 ml DMF followed by 1.115 ml triethylamine neat (1 eq., 0.81 g, 8 mmole). The reaction was stirred at room temperature for 24 hours then the DMF was removed in vacuo. The residue was taken up in 1N HCl ethyl acetate, extracted 3×with ethyl acetate, and the combined organic phase was dried over $MgSO_4$. The residue obtained after filtration and evaporation was then applied to a silica gel flash column pre-equilibrated with 6.5% methanol/methylene chloride and then eluted with 10% methanol/methylene chloride. The resultant colorless syrup yielded a soft white solid upon standing. $^1H$ NMR ($d_6$DMSO/TMS) δ: 2.31 (2H, t, J=6.21 Hz, $CH_2$), 2.42 (2H, t, J=6.77 Hz, $CH_2$) 2.84 (2H, t, J=6.93 Hz, $CH_2$), 3.29 (2H, q, J=6.37 Hz, $CH_2$), 3.86 (3H, s, $CH_3$), 8.01 ($^1H$, t, J=5.49 Hz, NH), 12.05 (1H, broad s, OH). $^{13}C$ NMR ($d_6$DMSO/TMS) δ: 29.07 ($CH_2$), 30.03 ($CH_2$), 37.6 (2$CH_2$), 55.85 ($CH_3$), 169.03 (Q), 171.24 (Q), 173.79 (Q).

EXAMPLE 5

Synthesis of (2-hydroxyethyldithio)ethylamidosuccinic acid

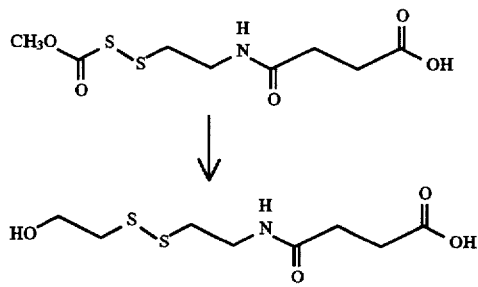

A round bottomed flask was charged with 399.6 mg (1 eq., 1.495 mmole) (methoxycarbonyldithio)ethylamidosuccinic acid dissolved in 5 ml methanol, cooled to 0° C., purged with argon, and then treated dropwise with a solution of 110.9 mg (0.95 eq., 995.9 µl, 1.42 mmole) mercaptoethanol in 4 ml methanol over a 30 min period. The stirred solution was allowed to warm to room temperature over 1 hour and then stirred at this temperature for an additional 3.5 hours, after which, the solvent was evaporated on the rotary evaporator (bath temp. 30° C.). The residue was subjected to vacuum transfer for 0.5 hours to ensure that all mercaptoethanol was removed. The resultant white solid was then titurated with 3 ml ether and then the solid was pumped on the high vacuum for 10 min. (bath temp. 40° C.) to yield approximately 0.3 g of (2-hydroxyethyldithio)ethylamidosuccinic acid as a pure white solid. $^1$H NMR ($d_6$DMSO/TMS) δ: 2.31 (2H, t, J=6.02 Hz, $CH_2$), 2.41 (2H, t, J=6.39 Hz, $CH_2$), 2.77 (4H, q, J=6.86 Hz, 2×$CH_2$), 3.35 (2H, t, J=6.75 Hz, $CH_2$), 3.60 (2H, t, J=6.46 Hz, $CH_2$), 8.06 (1H, t, NH). $^{13}$C NMR ($d_6$DMSO/TMS) δ: 30.53 ($CH_2$), 31.62 ($CH_2$), 38.46 ($CH_2$), 39.68 ($CH_2$), 42.11 ($CH_2$), 61.27 ($CH_2$), 174.76 (Q), 176.63 (Q).

EXAMPLE 6

Synthesis of N-(4-azido-2-nitrophenyl)-N'-(N-((2-hydroxyethyldithio)-2-ethylamidosuccinimido)-3-aminopropyl)-N'-methyl-1,3-propanediamine The reaction was carried out in the dark. A one necked flask was charged with 95.0 mg (1 eq., 0.375 mmole) (2-hydroxyethyldithio)ethylamidosuccinic acid in 1.5 ml DMF and this solution was then sequentially treated with 0.1154 g (1 eq., 0.375 mmole) N-(3-aminopropyl)-N'-(4-azido-2-nitrophenyl)-N-methyl-1,3-propanediamine in 2 ml methylene chloride, 57.5 µl, (1.1 eq., 41.74 mg, 0.4125 mmole) triethylamine (neat), and then 156.4 mg (1.1 eq., 0.4175 mmole) O-benzotriazol-1-yl-N,N,N',N'-tetramethyluronium hexafluorophosphate in 1 ml DMF. The reaction was monitored by TLC and found to be complete after 15 min at which time the solvents were removed via vacuum transfer (bath temp. 40° C.). The residue was purified by flash chromatography. $^1$H NMR ($CD_3CN$/TMS) δ: 1.17 (2H, t, J=7.29 Hz, $CH_2$), 1.71 (2H, m, J=6.88 Hz, $CH_2$), 1.89 (2H, t, J=6.99 Hz, $CH_2$), 2.37 (2H, t, J=3.10 Hz, $CH_2$), 2.40 (3H, s, $CH_3$), 2.64 (2H, t, J=7.45 Hz, $CH_2$), 2.69 (2H, t, J=7.27 Hz, $CH_2$), 2.76 (2H, t, J=6.69 Hz, $CH_2$), 2.80 (2H, t, J=5.33 Hz, $CH_2$), 3.01 (2H, q, J=7.31 Hz, $CH_2$), 3.16 (2H, q, J=6.42 Hz, $CH_2$), 3.40 (4H, m, J=6.48 Hz, 2×$CH_2$), 3.70 (2H, t, J=6.30 Hz, $CH_2$), 6.97 (2H, d, ArH), 7.18 (2H, dd, ArH), 7.77 (2H, d, NH), $^{13}$C NMR ($CD_3CN$/TMS) δ: 27.2 ($CH_2$), 27.8 ($CH_2$), 32.25 ($CH_2$), 32.28 ($CH_2$), 38.60 ($CH_2$), 38.80 ($CH_2$), 39.7 ($CH_2$), 42.2 ($CH_3$), 42.4 ($CH_2$), 42.5 ($CH_2$), 56.3 ($CH_2$), 56.4 ($CH_2$), 61.4 ($CH_2$), 116.6 (ArH), 117.3 (Ar), 128.9 (Q), 129.3 (Ar), 132.7 (Q), 144.6 (Q), 174.6 (C=O), 174.8 (C=O).

EXAMPLE 7

Synthesis of N-(4-azido-2-nitrophenyl)-N'-(N-((2-hydroxyethyldithio)-2-ethylamidosuccinimido)-3-aminopropyl)-N'-methyl-1,3-propanediamine citrate salt (Fasttag™ reagent)

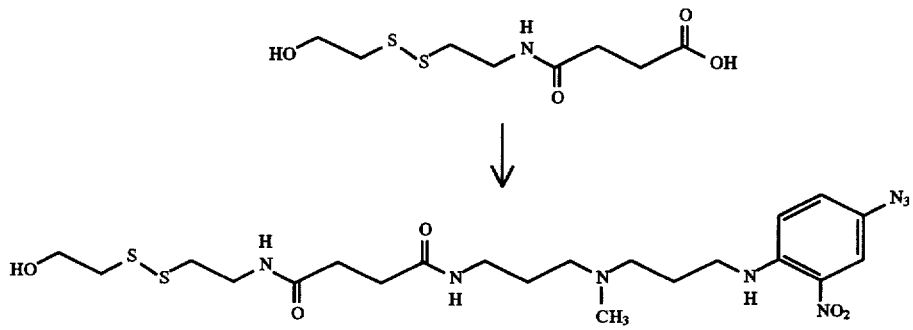

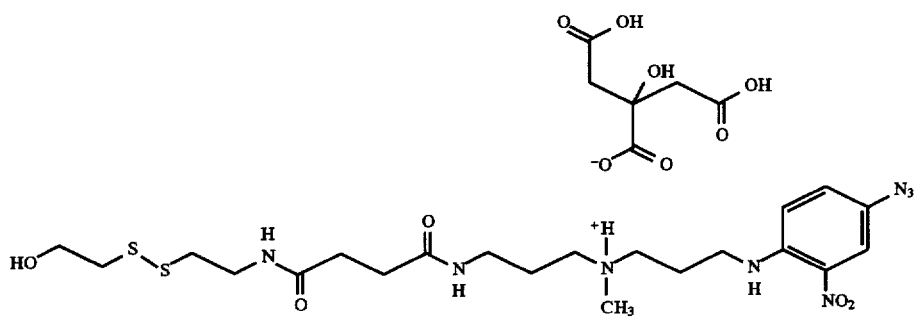

The reaction was carried out in the dark. A flask charged with a solution of 1.15 g (2.12 mmole) of N-(4-azido-2-nitrophenyl)-N'-(N-((2-hydroxyethyldithio)-2-ethylamidosuccinimido) -3-aminopropyl)-N'-methyl-1,3-propanediamine in a minimal amount of methanol was treated with a solution of 407.1 mg (2.12 mmole) citric acid dissolved in a minimal amount of methanol at room temperature. After stirring for 5 min the volatiles where removed in vacuo to give 1.4027 g of the desired product as a red solid.

EXAMPLE 8

Synthesis of Photoprobe® Thioctic Acid

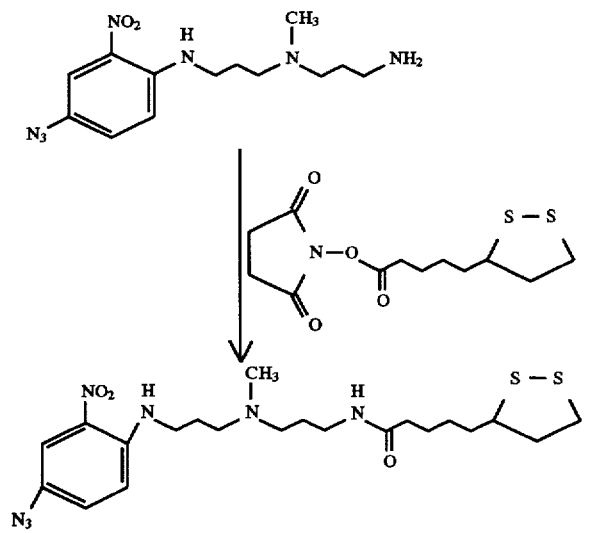

All operations were carried out in the dark. A one necked flask was charged with 360 mg (11.7 mmol) of N-(3-aminopropyl)-N'-(4-azido-2-nitrophenyl)-N-methyl-1,3-propanediamine dissolved in a solution containing 355.6 mg (11.7 mmol) thioctic acid-N-hydroxysuccinimide ester in 10 ml 7:3 pyridine/water and the solution was warmed to 37° C. for two hours. The solvent was removed in vacuo and the red oil was taken up in water and methylene chloride. The organic phase was separated, washed with brine, and dried over magnesium sulfate. After filtering off the drying agent and evaporating the solvent in vacuo, the red residue was applied to a silica gel flash column, eluting with 100% methanol. $^1$H NMR (CDCl$_3$/TMS) δ: 1.39 (1H, m, CH$_2$), 1.55 (4H, m, 2×CH$_2$), 1.82 (4H, m, 2×CH$_2$) 2.08 (2H, t, J=7.44 Hz, CH$_2$), 2.19 (3H, s, CH$_3$), 2.37 (2H, t, CH$_2$), 2.43 (2H, t, CH$_2$), 2.69 (1H, m, CH$_2$), 3.08 (1H, m, CH$_2$), 3.24 (2H, m, CH$_2$), 3.30 (2H, m, CH$_2$), 3.40 (1H, m, CH), 6.28 (1H, t, NH), 6.83 (1H, d, J=9.24 Hz, ArH), 7.07 (1H, dd, J=2.76 Hz, ArH), 7.78 (1H, d, J=2.69 Hz, ArH), 8.40 (1H, d, J=5.45 Hz, NH), $^{13}$C NMR (CDCl$_3$/TMS) δ: 172.61 (Q), 143.25 (Q), 131.30 (Q), 128.69 (CH), 127.49 (Q), 115.84 (CH), 115.41 (CH), 56.37 (CH), 56.14 (CH), 55.46 (CH$_2$), 41.97 (CH$_2$), 41.93 (CH$_3$), 40.13 (CH$_2$), 38.36 (CH$_2$), 38.30 (CH$_2$), 36.45 (CH$_2$), 34.51 (CH$_2$), 28.81 (CH$_2$), 26.54 (CH$_2$), 26.06 (CH$_2$), 25.34 (CH$_2$).

EXAMPLE 9

Synthesis of N-(4-azido-2-nitrophenyl)-N'-(N-(methoxycarbonyldithio)-2-ethylamidosuccinimido)-N'-methyl- 1,3-propanediamine

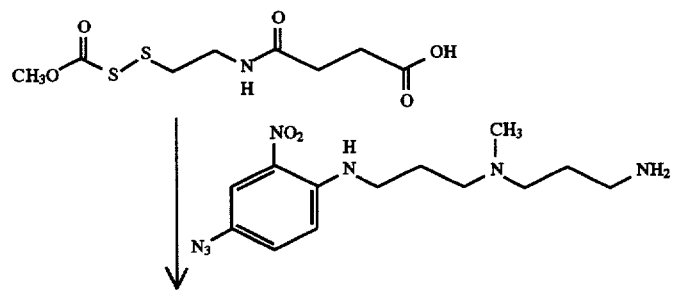

-continued

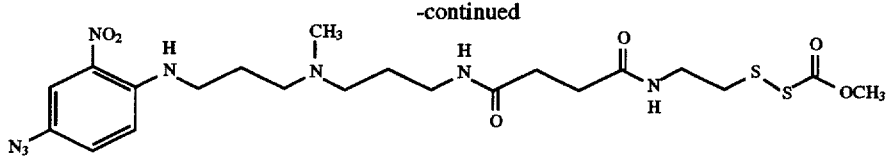

All operations were carried out in the dark. A round bottomed flask was charged with 166.3 mg (1 eq., 0.541 mmole) N-(3-aminopropyl)-N'-(4-azido-2-nitrophenyl)-nitrophenyl)-N-methyl-1,3-propanediamine in 3 ml anhydrous THF and this solution was then sequentially treated with 144.6 mg (methoxycarbonyldithio)ethylamidosuccinic acid (1 eq., 0.541 mmole) in 1 ml THF followed by 117.2 mg (1.05 eq., 0.568 mmole) dicyclohexylcarbodiimide. After stirring at room temperature for 5 hours the reaction was filtered and the filtrate evaporated in vacuo to give a red oil. The residue was dissolved in a minimal amount of methylene chloride and applied to a silica gel flash column that was pre-equilibrated with 8.5 % methanol/methylene chloride and eluted with the same solvent, collecting Rf=0.39 as a dark red oil.

EXAMPLE 10

Synthesis of (propyldithio)ethylamidosuccinic acid

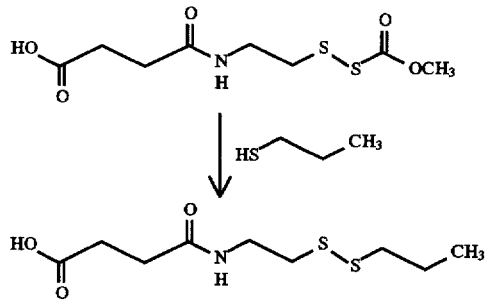

A flask was charged with 400 mg (1 eq., 1.5 mmole) of (methoxycarbonyldithio)ethylamidosuccinic acid dissolved in 5 ml methanol, cooled to 0° C., purged with argon, and then treated dropwise with a solution of 135.3 ml (114 mg, 1 eq., 1.5 mmole) propanethiol (purchased from Aldrich) in 4 ml of methanol over a 30 min. period. The reaction was then allowed to warm to room temperature and stirred for 18 hours. The volatiles were then removed by vacuum transfer and the residue applied to a flash silica gel column, eluting with 10% methanol/methylene chloride. $^1$H NMR ($d_6$DMSO/TMS) δ: 0.92 (3H, t, $CH_3$), 1.61 (2H, m, $CH_2$), 2.30 (2H, m, $CH_2$), 2.39 (2H, m, $CH_2$), 2.69 (2H, m, 2×$CH_2$), 3.31 (2H, m, 2×$CH_2$), 8.03 (1H, t, NH), 12.05 (1H, br. s, $CO_2$H). $^{13}$C NMR ($d_6$DMSO/TMS) δ: 173.65 (Q), 170.97 (Q), 39.83 ($CH_2$), 38.00 ($CH_2$), 37.10 ($CH_2$), 29.88 ($CH_2$), 28.99 ($CH_2$), 21.74 ($CH_2$), 12.67 ($CH_3$). $^1$H NMR ($CD_3$OD/TMS) δ: 0.98 (3H, t, J=7.33 Hz, $CH_3$), 1.69 (2H, h, J=7.22 Hz, $CH_2$), 2.47 (2H, m with fine splitting, $CH_2$), 2.56 (2H, m with fine splitting, $CH_2$), 2.68 (2H, t, J=7.15 Hz, $CH_2$), 2.77 (2H, t, J=6.84 Hz, $CH_2$), 3.46 (2H, t, J=6.84 Hz, $CH_2$). $^{13}$C NMR ($CD_3$OD/TMS) δ: 176.72 (Q), 174.75 (Q), 41.87 ($CH_2$), 39.87 ($CH_2$), 38.42 ($CH_2$), 31.77 ($CH_2$), 30.72 ($CH_2$), 23.47 ($CH_2$), 13.40 ($CH_3$).

EXAMPLE 11

Synthesis of N-(4-azido-2-nitrophenyl)-N'-((N-(propyldithio)-2-ethylamidosuccinimido)-3-aminopropyl)-N'-methyl-1,3-propanediamine

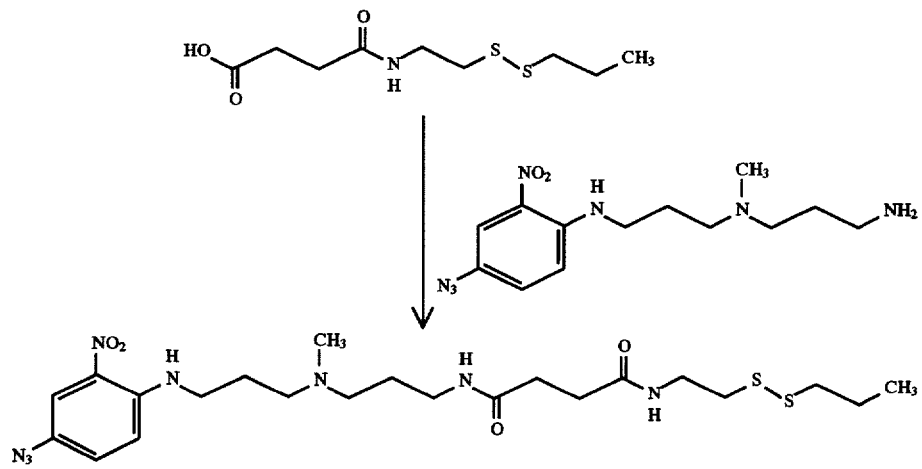

EXAMPLE 12

Synthesis of (2-acetamidoethyldithio)ethylamidosuccinic acid

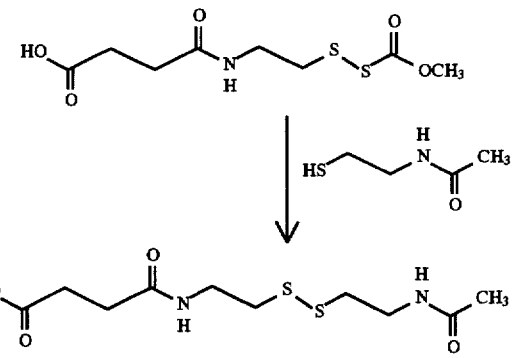

A flask was charged with 1000 mg (1.05 eq., 3.74 mmole) of (methoxycarbonyldithio)ethylamidosuccinic acid dissolved in 12.5 ml methanol, cooled to 0° C., purged with argon, and then treated dropwise with a solution of 379 ml (424.6 mg, 1 eq., 3.56 mmole) propanethiol in 10 ml of methanol over a 30 min. period. The reaction was then allowed to warm to room temperature and stirred for 18 hours. The volatiles were then removed by vacuum transfer and the residue applied to a flash silica gel column, eluting with 17.5% methanol/methylene chloride. $^1$H NMR (CD$_3$OD/TMS) δ: 1.95 (3H, t, J=7.33 Hz, CH$_3$), 2.49 (2H, m, CH$_2$), 2.58 (2H, m, CH$_2$), 2.81 (4H, m, 2×CH$_2$), 3.47 (4H, m, 2×CH$_2$). $^{13}$C NMR (CD$_3$OD/TMS) δ: 176.67 (Q), 174.77 (Q), 173.44 (Q), 39.68 (2×CH$_2$), 38.49 (CH$_2$), 38.43 (CH$_2$), 31.66 (CH$_2$), 30.60 (CH$_2$), 22.65 (CH$_2$).

EXAMPLE 13

Synthesis of N-(4-azido-2-nitrophenyl)-N'-((N-(2-acetamidoethyldithio)-2-ethylamidosuccinimido)-3-aminopropyl-N'-methyl-1,3-propanediamine

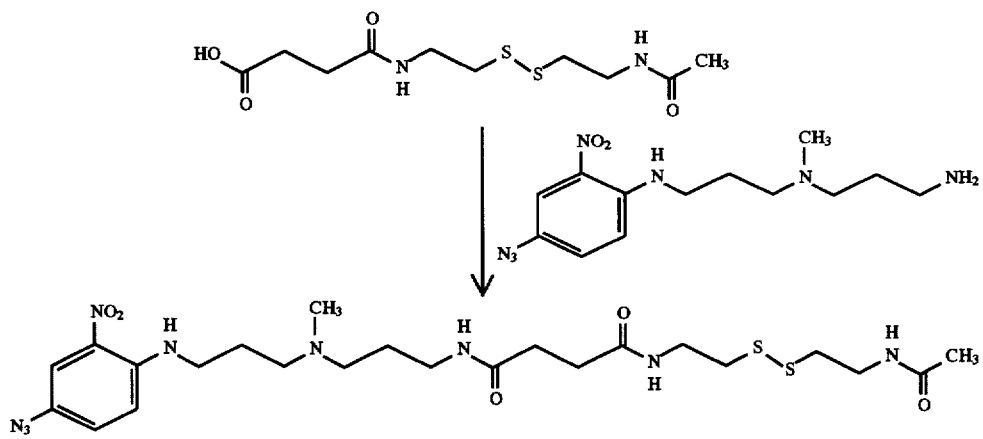

All operations were carried out in the dark. A one necked flask was charged with 231 mg (1.33 eq., 0.753 mmole)N-

All operations were carried out in the dark. A one necked flask was charged with 138 mg (1.33 eq., 0.45 mmole) of N-(3-aminopropyl)-N'-(4-azido-2-nitrophenyl)-N -methyl-1,3-propanediamine in 0.3 ml DMF, and then sequentially treated with 85 mg (1 eq., 0.338 mmole) (propyldithio)ethylamidosuccinic acid in 0.3 ml DMF, 128 mg (1 eq., 0.338 mmole) O-benzotriazol-1-yl-N,N,N',N'-tetramethyluronium hexafluorophosphate (Aldrich) in 2 ml DMF, and then 47.1 ml (34.2 mg, 1 eq., 0.338 mmol) of triethylamine (neat). The reaction was stirred at room temp. for 1.5 hours and then the volatiles were removed by vacuum transfer. The crude material was purified by applying to a flash silica gel column, eluting with 15% methanol/methylene chloride. $^1$H NMR (CD$_3$OD/TMS) δ: 0.97 (3H, t, J=7.35 Hz, CH$_3$), 1.68 (2H, h, J=7.25 Hz, CH$_2$), 1.90 (2H, p, CH$_2$), 2.10 (2H, p, CH$_2$), 2.48 (4H, m, CH$_2$), 2.66 (2H, t, J=7.15 Hz, CH$_2$), 2.75 (2H, t, CH$_2$), 2.86 (3H, s, CH$_3$), 3.15 (4H, m 2×CH$_2$), 3.43 (4H, t, J=6.82 Hz, CH$_2$), 3.51 (2H, t, J=6.87 Hz, CH$_2$), 7.12 1H, d, J=9.21 Hz, ArH), 7.26 (1H, dd, J=2.71, 9.21 Hz, ArH), 7.74 (1H, d, J=2.65 Hz, ArH). $^{13}$C NMR (CD$_3$OD/TMS) δ: 176.05 (Q), 174.65 (Q), 144.17 (2×, Q), 133.06 (Q), 129.33 (CH), 117.28 (CH), 116.68 (CH), 55.45 (CH$_2$), 55.18 (CH$_2$), 41.77 (CH$_2$), 41.13 (CH$_2$), 40.50 (CH$_3$), 39.73 (CH$_2$), 38.39 (CH$_2$), 36.95 (CH$_2$), 31.94 (CH$_2$), 31.75 (CH$_2$), 26.16 (CH$_2$), 25.18 (CH$_2$), 23.42 (CH$_2$), 13.33 (CH$_3$).

(3-aminopropyl)-N'-(4-azido-2-nitrophenyl)-N -methyl-1,3-propanediamine in 0.5 ml DMF, and then sequentially treated with 166 mg (1 eq., 0.566 mmole) (2-acetamidoethyldithio)ethylamidosuccinic acid in 0.5 ml DMF, 214.6 mg (1 eq., 0.566 mmole) O-benzotriazol-1-yl-N,N,N',N'-tetramethyluronium hexafluorophosphate (Aldrich) in 3.3 ml DMF, and then 79 ml (57.3 mg, 1 eq., 0.566 mmol) of triethylamine (neat). The reaction was stirred at room temperature for 2.5 hours and then the volatiles were removed by vacuum transfer. The crude material was purified by applying to a flash silica gel column, eluting with 12.5% methanol/methylene chloride. $^1$H NMR (CD$_3$OD/TMS) δ: 1.87 (2H, t, CH$_2$), 1.96 (3H, s, CH$_3$), 2.07 (2H, t, CH$_2$), 2.50 (4H, m, 2×CH$_2$), 2.69 (3H, s, CH$_3$), 2.81 (4H, m, 2×CH$_2$), 2.96 (2H, t, CH$_2$), 3.04 (2H, t, CH$_2$), 3.26 (2H, t, CH$_2$), 3.47 (2H, t, CH$_2$), 7.16 (1H, d, J=9.25 Hz, ArH), 7.30 (1H, dd, J=2.69, 9.22 Hz, ArH), 7.81 (1H, d, J=2.69 Hz, ArH). $^{13}$C NMR (CD$_3$OD/TMS) δ: 175.72 (Q), 174.89 (Q), 173.58 (Q), 144.36 (Q), ~33.5 (Q), 129.40 (CH), 129.24 (Q), 117.40 (CH), 116.66 (CH), 55.61 (CH$_2$), 55.50 (CH$_2$), 41.43 (CH$_2$), 40.99 (CH$_3$), 39.78 (CH$_2$), 39.71 (CH$_2$), 38.53 (CH$_2$), 38.47 (CH$_2$), 37.49 (CH$_2$), 32.12 (CH$_2$), 32.00 (CH$_2$), 26.43 (CH$_2$), 25.67 (CH$_2$), 22.64 (CH$_3$).

EXAMPLE 14

Synthesis of N-(4-azido-2-nitrophenyl)-N'-((N-(2-pyridyldithio)-3-propionyl)-3-aminopropyl) -N'-methyl- 1,3-propanediamine (2H, p, J=6.53 Hz, CH$_2$), 2.17 (3H, s, CH$_3$), 2.47 (4H, 2 overlapping t, 2×CH$_2$), 2.57 (2H, t, J=6.81 Hz, CH$_2$), 3.06 (2H, t, J=6.80 Hz, CH$_2$), 3.35 (4H, m, 2×CH$_2$), 6.89 (1H, d, J=9.44 Hz, ArH), 6.99 (1H, t, NH), 7.10 (2H, m, J=2.79 Hz, ArH), 7.64 (2H, m, ArH), 7.82 (1H, d, J=2.73 Hz, ArH), 8.44 (2H, m, ArH). $^{13}$C NMR (CDCl$_3$/TMS) δ: 170.55 (Q), 159.64 (Q), 149.56 (CH), 143.31 (Q), 137.08 (CH), 131.43 (Q), 128.22 (CH), 127.56 (Q), 120.93 (CH), 120.07 (CH), 115.94 (CH), 115.55 (CH), 56.20 (CH$_2$), 55.66 (CH$_2$), 42.09 (CH$_2$), 41.99 (CH$_3$), 38.55 (CH$_2$), 35.78 (CH$_2$), 34.70, 26.67 (CH$_2$), 26.27 (CH$_2$).

EXAMPLE 15

Photocoupling of Fasttag™ Reagent to a Nucleic Acid

Fasttag™ reagent was reconstituted with 500 μl deionized H$_2$O to give a final concentration of 1 mg/ml. To a known volume (up to 100 μl at 0.5 μg/μl) of λ Hind III DNA in water was added an equal volume of the Fasttag™ solution. The reaction tube was placed with the cap open into an ice bath and irradiated for 15 min with a mercury vapor lamp positioned 10 cm above the reaction tube. Following irradiation, the DNA/Fasttag™ solution was brought to 200 μl with deionized H$_2$O and 200 μl of 0.1M Tris pH 9.5 was added to the photolabeling reaction. 400 μl of 2-butanol was added to the DNA/Fasttag™ solution, vortexed vigorously, and centrifuged to separate the phases. The upper butanol phase was removed and discarded. The aqueous phase was extracted with an additional 400 μl of 2-butanol, again discarding the butanol layer following centrifugation.

EXAMPLE 16

Reduction of Fasttag™ reagent

In order to achieve removal of the protecting group, a reduction reaction was carried out. To 40 μl of Fasttag™-

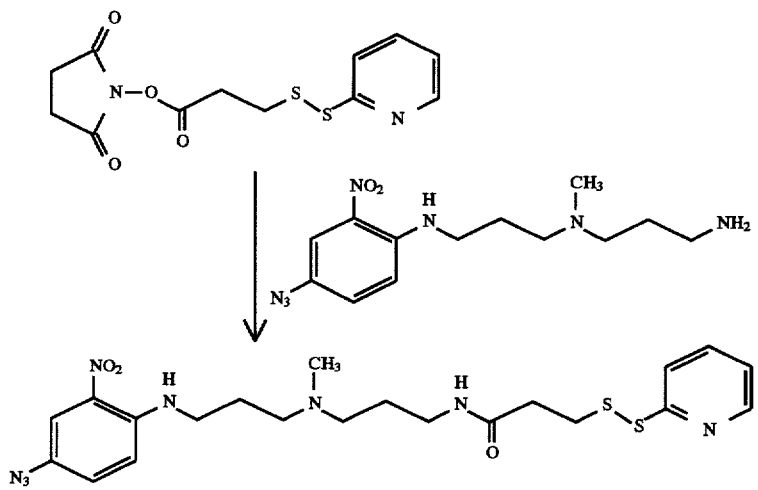

A round bottomed flask, covered with tin foil to exclude light was charged with 98.4 mg (1 eq., 0.32 mmol) of N-(3-aminopropyl)-N'-(4-azido-2-nitrophenyl)-N-methyl-1,3-propanediamine in 5 ml 7:3 pyridine/water. To this, 100 mg (1 eq., 0.32 mmol) of SPDP was added to the stirred solution and warmed to 37° C. for 2 hours, after which the pyridine was removed in vacuo. The resultant red aqueous solution was diluted with an equal volume of 0.5M NaHCO$_3$ then extracted 2× with ethyl acetate and dried over MgSO$_4$. After filtering, and evaporating the solution, the residue was applied to a silica gel flash column, eluting with 1:3:296 of triethylamine/water/MeOH to yield 99.8 mg as a red oil. $^1$H NMR (CDCl$_3$/TMS) δ: 1.72 (2H, p, J=6.75 Hz, CH$_2$), 1.87

DNA in H$_2$O (≦50 μg total DNA) was added 5 μl of 1.0M Na Citrate, pH 5.5. Following this, 5 μl of 20 mM TCEP (Pierce) in 0.1M HCl was added and incubated at room temperature for 10 min.

EXAMPLE 17

Fluorescein-maleimide coupling to Fasttag™ reagent thiols

The following components were added to the 50 μl reduction reaction from Example 9 to give a final volume of 100 μl:

30 μl H$_2$O

10 μl 0.5M Tris-HCl, pH 9.5

10 μl 0.5M fluorescein-maleimide (Molecular Probes) in DMSO.

The maleimide coupling reaction was allowed to proceed in darkness for 10 min at 65° C. The Fasttag™-fluorescein (FL)-labeled DNA was precipitated away from unincorporated fluorescein-maleimide by adding the following components to the 100 μl fluorescein-maleimide coupling reaction:

100 μl $H_2O$

50 μl 10M ammonium acetate

625 μl 100% ethanol

The mixture was incubated at –80° C. for 15 min. The precipitated DNA was pelleted by centrifugation at 13,000×g in a microcentrifuge. The pelleted DNA was resuspended in $H_2O$ or 1×TE to give an appropriate working stock concentration.

EXAMPLE 18

Dot Blot of Fasttag™-FL-labeled λ Hind III DNA

Fasttag™-FL-labeled λ Hind III DNA (Fasttag™-FL-DNA) was resuspended in 1×TE at 20 ng/μl. A series of 10-fold serial dilutions of Fasttag™-FL-DNA was prepared as follows:

| Dilution # | | Final Concentration |
| --- | --- | --- |
| 1. | 5 μl of Fasttag™-FL-DNA + 45 μl of 6x SSC | 2.0 ng/μl |
| 2. | 5 μl of Dilution #1 + 45 μl of 6x SSC | 0.2 ng/μl |
| 3. | 5 μl of Dilution #2 + 45 μl of 6x SSC | 20.0 pg/μl |
| 4. | 5 μl of Dilution #3 + 45 μl of 6x SSC | 2.0 pg/μl |
| 5. | 5 μl of Dilution #4 + 45 μl of 6x SSC | 0.2 pg/μl |
| 6. | 5 μl of Dilution #5 + 45 μl of 6x SSC | 0.02 pg/μl |

5 μl of each dilution was dotted onto a nitrocellulose membrane (Schleicher & Schuell) and crosslinked by incubation at 80° C. in a vacuum oven for 2 hours. The membrane was blocked by washing 3×10 min in at least 1 ml/$cm^2$ of phosphate-buffered saline, 0.4% w/v casein, 0.1% (v/v) Tween 20, pH 7.4 (blocking buffer). Goat anti-fluorescein conjugated to alkaline phosphatase was dissolved at 0.83 μg/ml in blocking buffer. The membrane was incubated at 0.3 ml/$cm^2$ in the antibody solution for 30 min at room temperature. The membrane was washed 3×10 min in phosphate-buffered saline, 0.1% (v/v) Tween 20 (PBST) and equilibrated for 5 min in 0.1M Tris 9.5. Two drops each of Vector® BCIP/NBT substrate kit components 1, 2, and 3 (Vector) were dropped into 5 ml of 0.1M Tris 9.5 and the membrane was incubated at 0.1 ml/$cm^2$ in substrate for 15 min. The membrane was washed in deionized $H_2O$ for 5 min to terminate the color reaction. Dots were visible out to the one containing 1 pg of DNA.

EXAMPLE 19

Southern hybridization of λ Hind III DNA using Fasttag™-FL-labeled λ Hind III DNA (Fasttag™-FL-DNA)

100 ng of λ Hind III DNA were mixed with 10 μl of 1×TE and 4 μl of loading solution and loaded on a 0.9% agarose gel. The gel was run in 1.0×TBE at 10 V/cm and blotted onto nitrocellulose using standard methods. The membrane was cross-linked by incubation in a vacuum oven at 80° C. for 2 hours and then prehybridized in a hybridization bag containing 0.3 ml/$cm^2$ hybridization solution (0.25 M $Na_2HPO_4$, pH 7.2, 45% (v/v) formamide, 7% (w/v) sodium dodecyl sulfate (SDS), 1.0 mM EDTA) at 42° C. for 18 hours. The prehybridization solution was discarded and replaced with the same volume of fresh hybridization solution. Fasttag™-FL-DNA at a concentration of 250 ng/100 μl was denatured at 100° C. for 5 min on a heating block and added to hybridization solution to a final concentration of 25 ng/ml. The bag was sealed and incubated at 42° C. for 18 hours. Following hybridization, the membrane was washed 2×5 min in 2×SSC, 1.0% (w/v) SDS at room temperature; 2×15 min in 0.2×SSC, 1.0% (w/v) SDS at 65° C.; 2×5 min in 1×SSC at room temperature. The bound Fasttag™ reagent-FL-DNA was detected as outlined in Example 11. All the expected bands of DNA were visualized by the colorimetric detection.

EXAMPLE 20

Biotin-maleimide coupling to Fasttag™ reagent thiols

The following components were added to the 50 μl reduction reaction from Example 9 to give a final volume of 100 μl:

30 μl $H_2O$

10 μl 0.5M Tris-HCl, pH 9.5

10 μl 0.5M biotin-maleimide (Vector) in DMSO

The maleimide coupling reaction was allowed to proceed for 10 min at 65° C. The Fasttag™-biotin (B)-labeled DNA was precipitated away from unincorporated biotin-maleimide by adding the following components to the 100 μl biotin-maleimide coupling reaction:

100 μl $H_2O$

50 μl 10M ammonium acetate

625 μl 100% ethanol.

The mixture was incubated at –80° C., for 15 min. The precipitated DNA was pelleted by centrifugation at 13,000×g in a microcentrifuge. The pelleted DNA was resuspended in $H_2O$ or 1×TE to give an appropriate working stock concentration.

EXAMPLE 21

Dot Blot of Fasttag™-B-labeled λ Hind III DNA

Fasttag™-B-labeled λ Hind III DNA (Fasttag™-B-DNA) was resuspended in 1×TE at 20 ng/μl. A series of 10-fold serial dilutions of Fasttag™-B-DNA was prepared as follows:

| Dilution # | | Final Concentration |
| --- | --- | --- |
| 1. | 5 μl of Fasttag™-B-DNA + 45 μl of 6x SSC | 2.0 ng/μl |
| 2. | 5 μl of Dilution #1 + 45 μl of 6x SSC | 0.2 ng/μl |
| 3. | 5 μl of Dilution #2 + 45 μl of 6x SSC | 20.0 pg/μl |
| 4. | 5 μl of Dilution #3 + 45 μl of 6x SSC | 2.0 pg/μl |
| 5. | 5 μl of Dilution #4 + 45 μl of 6x SSC | 0.2 pg/μl |
| 6. | 5 μl of Dilution #5 + 45 μl of 6x SSC | 0.02 pg/μl |

5 μl of each dilution was dotted onto a nitrocellulose membrane and crosslinked by incubation at 80° C., in a vacuum oven for 2 hours. The membrane was blocked by washing 3×10 min in at least 1 ml/$cm^2$ of Tris-buffered saline, 0.1% (v/v) Tween 20, pH 7.4 (TBST). VECTASTAIN® ABC-AP reagent (Vector) was prepared in TBST as described in the manufacturer's instructions. ABC-AP is a pre-formed complex of avidin and biotinylated alkaline phosphatase which retains binding sites for biotin and as such binds to biotinylated macromolecules, attaching alkaline phosphatase to them. The membrane was incubated at 0.3 ml/cm² in the ABC-AP reagent for 30 min at room temperature. The membrane was washed 3×10 min in TBST and equilibrated for 5 min in 0.1M Tris 9.5. Two drops each of Vector® BCIP/NBT substrate kit components 1, 2, and 3 were dropped into 5 ml of 0.1M Tris 9.5 and the membrane was incubated at 0.1 ml/cm² in substrate for 15 min. The membrane was washed in deionized H₂O for 5 min to terminate the color reaction. Dots were visible out to the one containing 1 pg of DNA.

EXAMPLE 22

Fucose-maleimide coupling to Fasttag™ reagent thiols

The following components were added to the 50 µl reduction reaction from Example 9 to give a final volume of 100 µl:

30 µl H₂O

10 µl 0.5M Tris-HCl pH 9.5

10 µl 0.5M fucose-maleimide (Vector) in DMSO.

The maleimide coupling reaction was allowed to proceed in darkness for 10 min at 65° C. The Fasttag™-fucose (FC)-labeled DNA was precipitated away from unincorporated fucose-maleimide by adding the following components to the 100 µl fucose-maleimide coupling reaction:

100 µl H₂O

50 µl 10M ammonium acetate

625 µl 100% ethanol.

The mixture was incubated at −80° C., for 15 min. The precipitated DNA was pelleted by centrifugation at 13,000×g in a microcentrifuge. The pelleted DNA was resuspended in H₂O or 1×TE to give an appropriate working stock concentration.

EXAMPLE 23

Dot Blot of Fasttag™-FC-labeled λ Hind III DNA

Fasttag™-FC-labeled λ Hind III DNA (Fasttag™-FC-DNA) was resuspended in 1×TE at 20 ng/µl. A series of 10-fold serial dilutions of Fasttag™-FC-DNA was prepared as follows:

| Dilution # | | Final Concentration |
|---|---|---|
| 1. | 5 µl of Fasttag™-FL-DNA + 45 µl of 6x SSC | 2.0 ng/µl |
| 2. | 5 µl of Dilution #1 + 45 µl of 6x SSC | 0.2 ng/µl |
| 3. | 5 µl of Dilution #2 + 45 µl of 6x SSC | 20.0 pg/µl |
| 4. | 5 µl of Dilution #3 + 45 µl of 6x SSC | 2.0 pg/µl |
| 5. | 5 µl of Dilution #4 + 45 µl of 6x SSC | 0.2 pg/µl |
| 6. | 5 µl of Dilution #5 + 45 µl of 6x SSC | 0.02 pg/µl |

Five µl of each dilution was dotted onto a nitrocellulose membrane and crosslinked by incubation at 80° C., in a vacuum oven for 2 hours. The membrane was blocked by washing 3×10 min in at least 1 ml/cm² of phosphate-buffered saline, 0.4% casein, 0.1% (v/v) Tween 20, pH 7.4 (blocking buffer). Biotinylated *Aleuria aurantia* lectin (Vector) was dissolved in PBST at 5 µg/ml. The membrane was incubated at 0.3 ml/cm² in the lectin solution for 30 min at room temperature. The membrane was washed 3×10 min in PBST. VECTASTAIN® ABC-AP reagent was prepared in TBST as described in the manufacturer's instructions. The membrane was incubated at 0.3 ml/cm² in the ABC-AP reagent for 30 min at room temperature. The membrane was washed 3×10 min in TBST and equilibrated for 5 min in 0.1M Tris 9.5. Two drops each of Vector® BCIP/NBT substrate kit components 1, 2, and 3 were dropped into 5 ml of 0.1M Tris 9.5 and the membrane was incubated at 0.1 ml/cm² in substrate for 15 min. The membrane was washed in deionized H₂O for 5 min to terminate the color reaction. Dots were visible out to the one containing 10 pg of DNA.

We claim:

1. A method for modifying a nucleic acid comprising:

a. contacting a nucleic acid with a pro-thiol aryl azide having the structure:

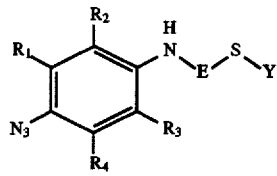

and salts thereof wherein, $R_1$ to $R_4$, which may be the same or different, are selected from the group consisting of H, alkyl, nitro, hydroxy, halide, carboxylic acid, methoxy, cyano, and amino groups;

wherein E is a chain of $C_1$–$C_{20}$ having chain constituents selected from the group consisting of alkyl, alkenyl, alkynyl and heteroatoms, said chain constituents having substituents selected from the group consisting of H, $C_1$–$C_6$ alkyl, aryl, ester, ether, amine, amide and halo groups; and wherein Y is a protecting group for protecting the sulfur moiety from chemical reaction and is removable so as to generate a thiol moiety; and b. subjecting the nucleic acid and the pro-thiol aryl azide to activation conditions sufficient to cause reaction therebetween resulting in modifying the nucleic acid.

2. The method of claim 1 wherein step b comprises photoactivating the pro-thiol aryl azide in the presence of the nucleic acid.

3. The method of claim 2 further comprising:

c. removing unreacted pro-thiol aryl azide; and d. removing the protecting group Y to form an intermediate having the structure:

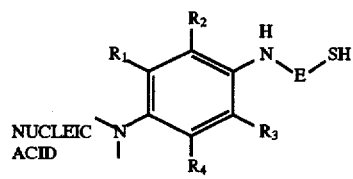

4. The method of claim 3 further comprising reacting the intermediate formed in step (d) with a label conjugated to a thiol-reactive group whereby a labeled nucleic acid results having the structure:

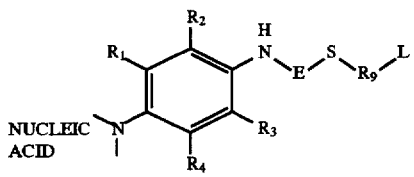

wherein $R_9$ is the thiolated conjugate of the thiol-reactive group and L is selected from the group consisting of a ligand or a detectable label.

5. The method of claim 4 wherein L is selected from the group consisting of fluorophores, biotin, fucose and haptens.

6. The method of claim 4 wherein the thiol-reactive group is selected from the group consisting of maleimides, iodoacetamides, pyridyl disulfides, vinyl pyridines, vinyl sulfones, acrylates, aryl mercurial compounds and aziridino compounds covalently linked to the detectable label or ligand.

7. The method of claim 6 wherein the thiol-reactive group is a maleimide and L is fluorescein.

8. A labeling kit for labeling a nucleic acid comprising:

a) a pro-thiol aryl azide having the structure:

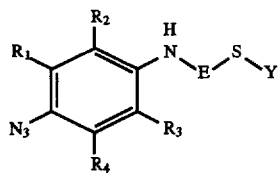

and salts thereof, wherein, $R_1$ to $R_4$, which may be the same or different, are selected from the group consisting of H, alkyl, nitro, hydroxy, halide, carboxylic acid, methoxy, cyano, amino groups;

wherein E is a chain of $C_1$–$C_{20}$ having chain constituents selected from the group consisting of alkyl, alkenyl, alkynyl and heteroatoms, said chain constituents having substituents selected from the group consisting of H, $C_1$–$C_6$ alkyl, aryl, ester, ether, amine, amide and halo groups; and wherein Y is a group capable of protecting the sulfur moiety from chemical reaction and removable so as to generate a thiol moiety b) a reagent to remove the protecting group so as to generate a terminal thiol; and c) a thiol-reactive label or ligand capable of reacting with the thiol.

9. The labeling kit of claim 8 wherein the pro-thiol aryl azide has the structure:

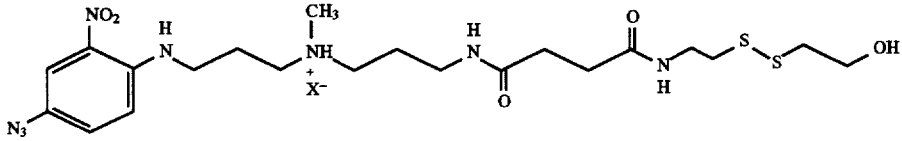

* * * * *